United States Patent [19]

Winter

[11] Patent Number: 5,302,745
[45] Date of Patent: Apr. 12, 1994

[54] PROCESS FOR THE PREPARATION OF ALKYL 3-OXO-2-PENTYL-1-CYCLOPENTENE ACETATES

[75] Inventor: Béat Winter, Sezenove/Bernex, Switzerland

[73] Assignee: Firmenich S.A., Geneva, Switzerland

[21] Appl. No.: 78,366

[22] Filed: Jun. 16, 1993

[30] Foreign Application Priority Data

Jul. 20, 1992 [CH] Switzerland .................... 2279/92

[51] Int. Cl.$^5$ ................ C07C 67/333; C07C 69/608; C07D 303/12
[52] U.S. Cl. .................................... 560/126; 549/546
[58] Field of Search ........................ 549/546; 560/126

[56] References Cited

U.S. PATENT DOCUMENTS 3,839,421 10/1974 Schwieter et al. ................ 560/126
4,076,947 2/1978 Schaub et al. .................... 549/546
5,216,183 6/1993 Sugiura et al. .................... 549/546

OTHER PUBLICATIONS

Chem. Abstracts, 99:175481d (1983).
A. Barco et al., "A New Synthesis of 2-Hydroxy-3-alkylcyclopent-2-en-1-ones", Synthesis, pp. 104-105 (Fed. 1975).
T. Shono et al., "Formation of α-Acetoxy Ketones and Synthesis of 2-Cyclopentenones", J. Am. Chem. Soc., 97:21 (1975).
U. Ravid et al., "New Synthesis in Dihydrojasmone Series", J. Org. Chem., 39: No. 17 (1974).
Alicyclic Compounds, 78:3798n (1973).
Chem. Abstracts, 76:3462g (1972).
Alicyclic Compounds, 75:109953n (1971).
Chem. Abstracts, 73:109363d (1970).
K. Sisido et al., "Synthesis of Methyl Dihydrojasmonate", P. & E.O.R., pp. 267-270 (1969).
A. Van der Gen, "Corps olfactifs a l'odeur de jasmin", Parf. Cosm. Sav. France, 2:8, pp. 356-370 (1969).
W. Wadsworth, Jr., et al., "The Utility Phosphonate Carbions in Olefin Synthesis", J. Am. Chem. Soc., 83:1733-38 (1961).

Primary Examiner—Joseph E. Evans
Attorney, Agent, or Firm—Pennie & Edmonds

[57] ABSTRACT

Process for the preparation of alkyl 3-oxo-2-pentyl-1-cyclopentene acetates starting from an epoxy-ester of formula

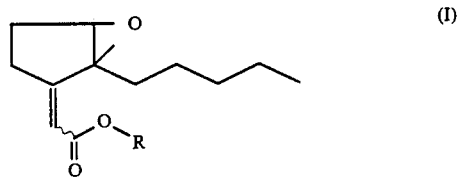

(I)

wherein R designates a lower linear or branched alkyl radical of $C_1$-$C_6$ and wherein the wavy line stands for a C—C bond of cis or trans configuration via an isomerization process.

7 Claims, No Drawings

PROCESS FOR THE PREPARATION OF ALKYL 3-OXO-2-PENTYL-1-CYCLOPENTENE ACETATES

BRIEF SUMMARY OF THE INVENTION

The instant invention provides a process for the preparation of alkyl 3-oxo-2-pentyl-1-cyclopentene acetates, which process is characterized by the isomerization of an epoxy-ester of formula

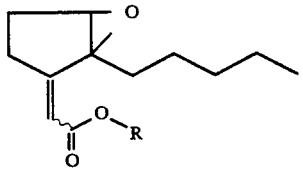

wherein R designates a lower linear or branched alkyl radical of $C_1$–$C_6$ and wherein the wavy line stands for a C—C bond of cis or trans configuration, by means of an acidic isomerization agent.

This invention relates further to an epoxy-ester of formula (I) and more particularly to methyl 2,3-epoxy-2-pentyl-1-cyclopentylidene acetate.

BACKGROUND OF THE INVENTION

It is known that the catalytic hydrogenation of methyl 3-oxo-2-pentyl-1-cyclopentene acetate, for example, by means of Pd/C in the presence of aluminum methoxide [see DE-OS 2,162,820] gives cis-methyl dihydrojasmonate, the floral odor note of which is particularly appreciated by perfumers.

The prior art reports a variety of syntheses of methyl 3-oxo-2-pentyl-1-cyclopentene acetate. Among them, only one utilizes an acyclic derivative in its last step [see Jap. Pat. 58 118,536; Chem. Abstracts 1983, 99 175481 d], whereas the others have as key-intermediates cyclic compounds. According to the nature of these latters, the known processes can be classified in 4 different categories:

a. via a gamma-lactone by rearrangement in the presence of polyphosphoric acid [Dutch Pat. 69 18,228; Chem. Abstracts 1971, 75, 109953 d];

b. via methyl dihydrojasmonate by bromination and dehydrobromination [Dutch Pat. 70 02,279; Chem. Abstracts 1972, 76, 3462 g] or by anodic oxidation of its enol-acetate [J. Am. Chem. Soc., 1975, 97, 6144];

c. via 2-pentyl-1,3-cyclopentanedione by reaction with dimethyl malonate [see e.g. DE-OS 2,008,833; Chem. Abstracts, 1970, 73, 109363 d];

d. via 2-pentyl-2-cyclopenten-1-one by radical addition of methyl dihydroxyacetate followed by dehydration [Parf. Cosm. Sav. France 1972, 2(8), 356]; by reaction with methyl diazoacetate [Perf. Essent. Oil Rec. 1969, 267; JP 70 00862], or by addition of methyl bromoacetate [J. Org. Chem. 1974, 39, 2637] or of methyl lithioacetate followed by oxidation with chromic acid.

None of the cited syntheses, mostly of academic interest, has found an industrial application for large scale production.

THE INVENTION

We have now discovered that alkyl 3-oxo-2-pentyl-1-cyclopentene acetates could be synthesized easily and efficiently by isomerizing, in the presence of an acidic isomerization agent, epoxy-esters of formula

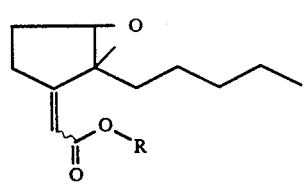

wherein symbol R and the wavy line have the meaning given above.

This process represents one of the objects of the instant invention.

Typically, acidic isomerization agents include mineral or organic protic acids or Lewis type acids. Specific examples of these agents are hydrochloric acid, sulfuric acid, phosphoric acid, p-toluenesulfonic acid or $BF_3$, $SnCl_4$ or $TiCl_4$. Acidic ion exchange resins can also be employed. The isomerization reaction takes place under mild conditions, an advantage which renders this process particularly attractive from the industrial viewpoint. In effect, temperatures of the order of 5°–30° C. are perfectly satisfactory for obtaining the desired products in excellent yields, up to 90% or even higher.

Epoxy-esters of formula (I), used as starting materials in the process of the invention, are compounds of novel structure and as such they also represent an object of the invention.

They can be prepared starting from 2,3-epoxy-2-pentyl-1-cyclopentanone, a known compound [see e.g. Synthesis, 1975, 104 ] via a process characterized by a Wittig type reaction, more precisely according to the method suggested by Wadsworth and Emmons [see J. Am. Chem. Soc. 1961, 83, 1733] as illustrated by the following reaction scheme:

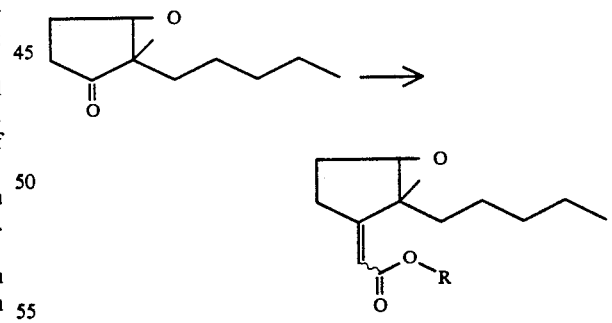

The reaction is carried out by the addition of alkyl dialkylphosphono-acetate, for instance methyl dimethylphosphonoacetate, to give methyl 2,3-epoxy-2-pentyl-1-cyclopentylidene acetate. The reaction is effected by analogy with known methods described in the literature. A detailed description of the method followed is provided in the following section.

The invention is illustrated by the following examples wherein the temperatures are indicated in degrees centigrade and the abbreviations have the meaning common in the art.

EXAMPLE

Preparation of methyl 3-oxo-2-pentyl-1-cyclopentene acetate a) 2,3-epoxy-2-pentyl-1-cyclopentanone 20 ml of a 70% hydrogen peroxide in water (0.43M) followed by 1.12 g (0.02M) of potassium hydroxide (pellets) have been added at 10° under stirring to a solution of 60.8 g (0.36M) of 3-oxo-2-pentyl-1-cyclopentene in 100 ml of methanol. During the addition, the reaction increases to 25° and the reaction mixture is kept at that value during 1.5 h. A novel fraction of equal volume of hydrogen peroxide, respectively KOH, was added in 2 portions to the reaction mixture. The conversion rate is of about 75% after 4 h of reaction.

10 g (0.07M) of $K_2CO_3$ were then added in 2 portions to the obtained mixture in 2 h and the mixture was kept under stirring for 2 further hours at 25°. After extraction with $CH_2Cl_2$, the combined organic extracts were washed with water, dried over $Na_2SO_4$ and concentrated to give a residue which, upon distillation under reduced pressure, gave 41 g (yield: 61%) of the desired epoxy ketone in the form of a colorless liquid.

B.p. 73°/66 Pa.

b) methyl 2,3-epoxy-2-pentyl-1-cyclopentylidene acetate (by analogy with Synthesis 1983, 284)

27.6 g (0.15M) of trimethylphosphonoacetate in 200 ml of tetrahydrofurane (THF) were added dropwise at 10°–20° to a suspension of sodium hydride (7.3 g; 0.15M of a 50% dispersion in oil) prior washed with 30–50 petrol ether in 200 ml of THF. 15 min after the end of the addition, there was added, at 11°–15°, a solution of 10.2 g (0.056M) of the epoxy-ketone prepared according to letter a) above in 150 ml of THF. The mixture was kept under stirring during 16 h at 25° and poured then into 500 ml of water and finally extracted with ether. The combined organic extracts were washed with a saturated aqueous solution of NaCl, dried over $Na_2SO_4$ and concentrated. The obtained residue was distilled to give a fraction at B.p. 92°–103°/4 Pa of the desired epoxy-ester (11.9 g; yield: 93%; isomeric ratio trans/cis 94:5).

IR(film): 2930, 2850, 1715, 1655, 1430, 1340, 1300, 1190, 1170, 1150, 1020, 850 cm$^{-1}$ $^1$H-NMR(360 MHz,CDCl$_3$): 0.90(t, J=7, 3H); 1.32(m, 7H); 1.80(m, 2H); 2.00(m, 1H); 2.13(dd, J=8, 14, 1H); 2.38(m, 1H); 3.22(dd, J=9, 18, 1H); 3.73(s, 3H); 5.95(s, 1H) δ ppm $^{13}$C-NMR(90,5 MHz,CDCl$_3$): 162.9(s), 114.7(d), 100.7(s), 67.4(s), 65.0(d), 51.1(q), 31.9(t), 27.1(t), 27.0(t), 25.8(t), 24.7(t), 22.5(t), 13.9(q) δ ppm MS: 224(M+, 1), 208(2), 195(4), 167(100), 151(14), 139(24), 126(19), 107(20), 91(24), 79(40), 67(15), 55(20), 41(20).

c) methyl 3-oxo-2-pentyl-1-cyclopentene acetate 0.1 ml (1.9 mM) of concentrated sulfuric acid was added under stirring at 4° to a solution of the epoxy-ester prepared under letter b) above (8.6 g; purity: 79%, 30 mM) in 50 ml of ether. The mixture was kept under stirring while the temperature increased gradually until about 30°. After having been maintained at that temperature for 1 h, the mixture was diluted with ether, washed with a saturated aqueous solution of NaHCO$_3$ and NaCl, then dried over Na$_2$SO$_4$ and finally concentrated to give 7.7 g of residue. This latter gave by distillation in a bulb-to-bulb apparatus (0.04 mb, temp.=110°) 6.97 g (purity: 93%; yield: 95%) of methyl 3-oxo-2-pentyl-1-cyclopentene acetate, the analytical characters of which were the following:

IR(film): 2950, 2920, 2850, 1735, 1695, 1635, 1430, 1350, 1255, 1190, 1170, 1110, 1055, 1015, 990 cm$^{-1}$ $^1$H-NMR(360 MHz, CDCl$_3$): 0.88(t, J=7, 3H); 1.2–1.4(m, 6H); 2.18(t, J=7, 2H); 2.41(m, 2H); 2.62(m, 2H) δ ppm $^{13}$C-NMR(90,5 MHz, CDCl$_3$): 209.2(s), 169.6(s), 163.5(s), 143.3(s), 52.3(q), 36.6(t), 34.4(t), 31.8(t), 29.7(t), 28.0(t), 23.2(t), 22.5(t), 13.0(q) δ ppm MS: 224(M+, 0,5), 206(2), 168(14), 151(100), 135(12), 121(17), 109(55), 108(47), 93(33), 79(42), 67(13), 55(19), 41(28).

What I claim is:

1. A process for preparing alkyl 3-oxo-2-pentyl-1-cyclopentene acetates, which comprises isomerizing by means of acidic isomerization agent an epoxy-ester of formula

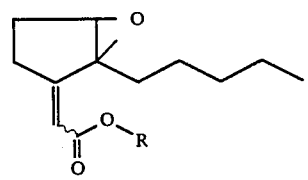

wherein R designates a lower linear or branched alkyl radical of $C_1$–$C_6$ and wherein the wavy line stands for a C—C bond of cis or trans configuration.

2. A process according to claim 1, wherein the epoxy-ester of formula (I) is methyl 2,3-epoxy-2-pentyl-1-cyclopentylidene acetate and the product obtained is methyl 3-oxo-2-pentyl-1-cyclopentene acetate.

3. A process according to claim 1, wherein the acidic isomerization agent is a mineral or an organic protic acid or a Lewis type acid, or an acidic ion exchange resin.

4. A process according to claim 3, wherein the protic acid is sulfuric acid.

5. A process according to claim 1, wherein the isomerization is carried out at a temperature of about 5°–30°.

6. An epoxy-ester of formula

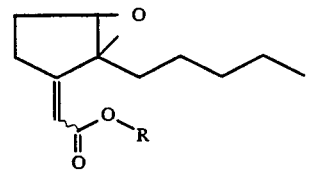

wherein R designates a lower linear or branched alkyl radical of $C_1$–$C_6$ and wherein the wavy line stands for a C—C bond of cis or trans configuration.

7. An epoxy-ester according to claim 6, wherein R represents a methyl radical.

* * * * *